US00PP08937P

United States Patent [19]

Trees

[11] Patent Number: Plant 8,937

[45] Date of Patent: Oct. 11, 1994

[54] NEW GUINEA IMPATIENS NAMED BSR-266 APPLE STAR

[75] Inventor: Scott C. Trees, Arroyo Grande, Calif.

[73] Assignee: George J. Ball, Inc., West Chicago, Ill.

[21] Appl. No.: 135,543

[22] Filed: Oct. 14, 1993

[51] Int. Cl.[5] ..... A01H 5/00
[52] U.S. Cl. ..... Plt./87.6
[58] Field of Search ..... Plt. 87.6

*Primary Examiner*—James R. Feyrer
*Attorney, Agent, or Firm*—Burns, Doane, Swecker & Mathis

[57] ABSTRACT

A new and distinct New Guinea Impatiens cultivar named BSR-266 Apple Star is provided. This new cultivar was the result of a controlled breeding program wherein a plant designated BFP-154 (non-patented in the United States) was pollinated by a plant designated BFP-170 (non-patented in the United States). The new cultivar forms attractive medium-sized bicolored blossoms displaying an iridescent appearance having pale pink petals with red attachment points and mid-ribs producing a red star pattern. Shiny dark bronze-green foliage and a good basal branching character also are exhibited. The new variety can be readily distinguished from the Vulcain cultivar (U.S. Plant Pat. No. 7,570).

1 Drawing Sheet

SUMMARY OF THE INVENTION

The present invention comprises a new and distinctive Impatiens plant, botanically known as New Guinea Impatiens, and hereafter referred to by the cultivar name BSR-266 Apple Star.

The new cultivar is the product of a planned breeding program. More specifically, the breeding program which resulted in the production of the new cultivar was carried out in a controlled environment during 1990 at Arroyo Grande, Calif., U.S.A. The female parent (i.e., the seed parent) was a plant designated bFP-154 (non-patented in the United States) which exhibits red/white bicolored star-patterned blossoms with dark bronze-green foliage. The male parent (i.e., the pollen parent) was a plant designated BFP-170 (non-patented in the United States) which exhibits light lavender purple/white bicolored blossoms with dark-green foliage. Each of the parent plants was a proprietary line of Ball FloraPlant. The parentage of the new cultivar can be summarized as follows:

BFP-154×BFP-170.

The seeds resulting from the above pollination were sown and plantlets were obtained which were physically and biologically different from each other. Selective study resulted in the identification of a single plant of the new cultivar. This plant had star-patterned bicolored blossoms and initially was designated BSR-266.

It was found that the cultivar of the present invention:

(a) exhibits attractive bicolored pale pink/red star-patterned blossoms, (b) exhibits a good basal branching character, and (c) exhibits an open-branching compact small mounded growth habit.

The new cultivar forms pale pink blooms which may appear to be almost white when under bright light. Soft red venation creates the appearance of a start when directly facing the blooms.

Asexual reproduction of the new cultivar by terminal or stem cuttings taken during 1991 at Arroyo Grande, Calif., U.S.A., has demonstrated that the characteristics of the new cultivar as herein described are firmly fixed and are retained through successive generations of such asexual propagation.

The BSR-266 Apple Star cultivar has not been observed under all possible environmental conditions to date. Accordingly, it is possible that the phenotype may vary somewhat with variations in the environment, such as temperature, light intensity, and day length.

When the new cultivar of the present invention is compared to the Vulcain cultivar (U.S. Plant Pat. No. 7,570), it is found that the new variety exhibits a growth habit which is not as compact as that of the Vulcain cultivar and forms bicolored pale pink/red blossoms whereas the Vulcain cultivar forms bicolored medium pink/dark pink blossoms. The BSR-266 Apple Star cultivar has smaller foliage than the Vulcain cultivar. Also, the BSR-266 Apple Star cultivar is generally earlier to flower from rooted cuttings under greenhouse conditions than the Vulcain cultivar.

When plant material of the BSR-266 Apple Star cultivar is subjected to standard random amplified polymorphic DNA marker analysis (Rapd) using polymerase chain reaction (PCR) and a known unique set of DNA primers, it is found to exhibit a different fingerprint map when compared to that of the Vulcain cultivar which confirms its genetic distinctiveness.

Plants of the new BSR-266 Apple Star cultivar will be marketed under the Celebration trademark by George J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The color values were determined during the first week of April, 1993. The readings were taken at West Chicago, Ill., U.S.A. The plants were produced from cuttings taken from stock plants and were grown under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting Habit.*—Fibrous and branching.

Plant description:

*Form.*—Good basal branching.

*Habit of growth.*—Compact small mounded. A mature plant commonly measures approximately 19 to 20 cm. in height and approximately 21 to 22 cm. in width when greenhouse grown, and when field grown a height of approximately 26 to 27 cm. and a width of approximately 37 to 38 cm. In contrast the vulcain cultivar commonly measures approximately 16 to 17 cm. in height and 18 to 19 cm. in width when greenhouse grown, and when field grown a height of approximately 23 to 25 cm. and a width of approximately 35 to 37 cm.

*Foliage.*—The configuration is narrow and lanceolate. The leaves of the BSR-266 Apple Star cultivar commonly measure approximately 9 cm.×3.5 cm. while those of the Vulcain cultivar commonly measure approximately 10 cm.×3.5 cm. The foliage of the BSR-266 Apple Star cultivar commonly is Greyed-Purple Group 187B (abaxial) and Green Group 139A with veins of Greyed-Purple Group 187B (adaxial). This can be compared to Greyed-Purple Group 187B (abaxial) and Green Group 136A with veins of Greyed-Purple Group 187B (adaxial) and a central area of Yellow-Orange Group 22A for the Vulcain cultivar. The stem color is Greyed-Purple Group 183A which can be compared to Greyed-Purple Group 185A for the Vulcain cultivar.

Flower description:

*Flowering habit.*—Freely flowering, more freely flowering than the Vulcain cultivar.

*Natural flowering season.*—Year-round in greenhouse environment.

*Flowers borne.*—Above foliage, arising from leaf axils.

*Flower color.*—Red Group 49D with attachment points and mid-ribs of Red Group 50A producing a "star" pattern (abaxial) and Red Group 48B (adaxial). This can be compared to Red-Purple Group 65B with Red Group 43C "star" pattern (abaxial) and Red Group 43C (adaxial) for the Vulcain cultivar. The "star" pattern is more intense in both cultivars when grown under cool greenhouse conditions.

*Quantity of flowers.*—Approximately 5 to 10 per stem.

*Number of petals.*—Five.

*Flower diameter.*—Approximately 5.0 cm. which can be compared to approximately 5.5 cm. for the Vulcain cultivar.

*Nectary length.*—Approximately 6.0 cm. which can be compared to approximately 7.0 cm. for the Vulcain cultivar.

*Nectary color.*—Yellow-Green Group 145C which can be compared to Red Group 48A for the Vulcain cultivar.

*Reproductive organs.*—The anthers are fused together forming one organ that surrounds the pistil. Generally, the anthers shed pollen prior to the stigma becoming receptive. The pollen color is Yellow Group 10D compared with Yellow Group 11B for the Vulcain cultivar. The stigma color is Yellow Group 10D and can be compared to Yellow Group 10C exhibited by the Vulcain cultivar. The ovary color is Greyed-Purple Group 183B and can be compared to Green Group 143B exhibited by the Vulcain cultivar.

I claim:

1. A new and distinct cultivar of New Guinea Impatiens named BSR-266 Apple Star, substantially as herein shown and described, which:

(a) exhibits attractive bicolored pale pink/red star-patterned blossoms, (b) exhibits a good basal branching character, and (c) exhibits an open-branching compact small mounded growth habit.

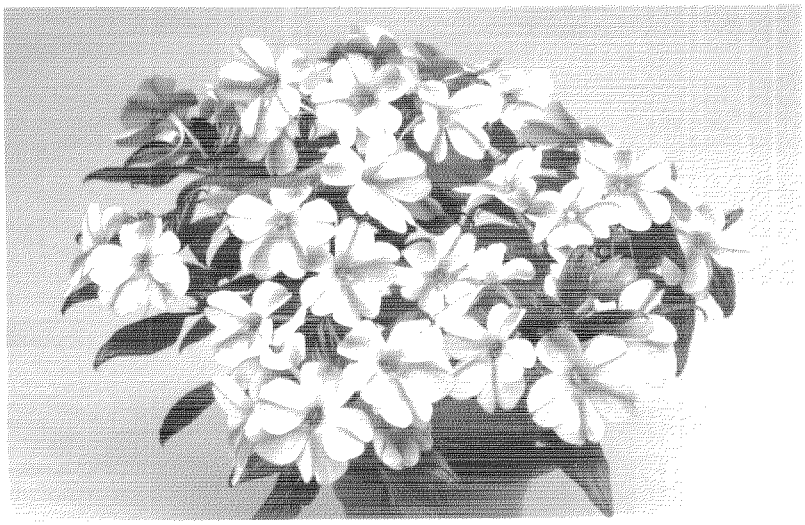

* * * * *